United States Patent [19]

Huang et al.

[11] Patent Number: 4,906,787

[45] Date of Patent: Mar. 6, 1990

[54] PROCESS FOR THE PRODUCTION OF ETHERS

[75] Inventors: Tracy J. Huang, Lawrenceville, N.J.; Charles M. Sorensen, Wilmington, Del.; Philip Varghese, Voorhees, N.J.

[73] Assignee: Mobil Oil Corporation, New York, N.Y.

[21] Appl. No.: 139,566

[22] Filed: Dec. 30, 1987

[51] Int. Cl.$^4$ ............................................. C07C 41/06
[52] U.S. Cl. .................................. 568/697; 511/198; 511/897
[58] Field of Search ....................... 568/697, 694, 698

[56] References Cited

U.S. PATENT DOCUMENTS 4,408,085 10/1983 Gottlieb et al. ..................... 568/697
4,714,787 12/1987 Bell et al. ............................ 568/697

FOREIGN PATENT DOCUMENTS 102840 3/1984 European Pat. Off. ............ 568/697
2187741 9/1987 United Kingdom ................ 568/697

Primary Examiner—Howard T. Mars
Attorney, Agent, or Firm—Alexander J. McKillop; Charles J. Speciale; Malcolm D. Keen

[57] ABSTRACT

Olefins undergo conversion in the presence of water and recycled alcohol to a mixture of alcohol and ether which is then subjected to various downstream operations including distillation and extraction or decantation to provide an ether-rich product containing little if any alcohol or water. The foregoing process is especially suitable to the conversion of propylene and propylene-containing streams to diisopropyl ether which is useful, inter alia, as an octane improver for gasoline.

29 Claims, 1 Drawing Sheet

PROCESS FOR THE PRODUCTION OF ETHERS

CROSS REFERENCE TO RELATED APPLICATIONS

This application is related to commonly assigned, copending U.S. patent application Ser. Nos. 139,570; 139,567; and, 139,576, each filed Dec. 30, 1987, which are concerned with the production of alcohol(s) and/or ether(s).

BACKGROUND OF THE INVENTION

This invention relates to a process for the production of ether(s). More particularly, the invention relates to a process for the conversion of a light olefin such as ethylene, propylene, butenes, pentenes, hexenes, heptenes, etc., and their mixtures, in a conversion unit employing an acidic zeolite as olefin conversion catalyst to produce a mixture of alcohol(s) and ether(s) and thereafter recovering the ether(s) containing at most only small amounts of co-produced alcohol(s) and water. The ether(s) are useful, inter alia, as high octane blending stocks for gasoline.

There is a need for an efficient catalytic process for manufacturing ethers from light olefins thereby augmenting the supply of high octane blending stocks for gasoline. Lower molecular weight ethers such as diisopropyl ether (DIPE) are in the gasoline boiling range and are known to have a high blending octane number. In addition, by-product propylene from which DIPE can be made is usually available in a fuels refinery. The petrochemicals industry also produces mixtures of light olefin streams in the $C_2$ to $C_7$ molecular weight range and the conversion of such streams or fractions thereof to ethers can also provide products which are useful as solvents and as blending stocks for gasoline.

The catalytic hydration of olefins to provide alcohols and ethers is a well-established art and is of significant commercial importance. Representative olefin hydration processes are disclosed in U.S. Pat. Nos. 2,162,913; 2,477,380; 2,797,247; 3,798,097; 2,805,260; 2,830,090; 2,861,045; 2,891,999; 3,006,970; 3,198,752; 3,810,849; and, 3,989,762, among others.

Olefin hydration employing zeolite catalysts is known. As disclosed in U.S. Pat. No. 4,214,107, lower olefins, in particular, propylene, are catalytically hydrated over a crystalline aluminosilicate zeolite catalyst having a silica to alumina ratio of at least 12 and a Constraint Index of from 1 to 12, e.g., HZSM-5 type zeolite, to provide the corresponding alcohol, essentially free of ether and hydrocarbon by-product.

According to U.S. Pat. No. 4,499,313, an olefin is hydrated to the corresponding alcohol in the presence of hydrogen-type mordenite or hydrogen-type zeolite Y, each having a silica-alumina molar ratio of 20 to 500. The use of such a catalyst is said to result in higher yields of alcohol than olefin hydration processes which employ conventional solid acid catalysts. Use of the catalyst is also said to offer the advantage over ion-exchange type olefin hydration catalysts of not being restricted by the hydration temperature. Reaction conditions employed in the process include a temperature of from 50°–300° C., preferably 100°–250° C., a pressure of 5 to 200 kg/cm$^2$ to maintain liquid phase or gas-liquid multi-phase conditions and a mole ratio of water to olefin of from 1 to 20. The reaction time can be 20 minutes to 20 hours when operating batchwise and the liquid hourly space velocity (LHSV) is usually 0.1 to 10 in the case of continuous operation.

European patent application No. 210,793 describes an olefin hydration process employing a medium pore zeolite as hydration catalyst. Specific catalysts mentioned are Theta-1, said to be preferred, ferrierite, ZSM-22, ZSM-23 and NU-10.

The reaction of light olefins with alcohols to provide ethers is also a well known type of process. According to U.S. Pat. No. 4,042,633, DIPE is prepared from isopropyl alcohol (IPA) employing montmorillonite clay catalysts, optionally in the presence of added propylene. U.S. Pat. No. 4,175,210 discloses the use of silicatungstic acid as catalyst for the reaction of olefin(s) with alcohol to provide ether(s). As disclosed in U.S. Pat. No. 4,182,914, DIPE is produced from IPA and propylene in a series of operations employing a strongly acidic cation exchange resin as catalyst. In the process for producing a gasoline blending stock described in U.S. Pat. No. 4,334,890, a mixed $C_4$ stream containing isobutylene is reacted with aqueous ethanol to form a mixture of ethyl tertiary butyl ether and tertiary butanol. U.S. Pat. No. 4,418,219 describes the preparation of methyl tertiary-butyl ether (MTBE), a high octane blending agent for motor fuels, by reacting isobutylene and methanol in the presence of, as catalyst, boron phosphate, blue tungsten oxide or a crystalline aluminosilicate zeolite having a silica to alumina mole ratio of at least 12:1 and a Constraint Index of from 1 to about 12 as catalyst. U.S. Pat. No. 4,605,787 discloses the preparation of alkyl tert-alkyl ethers such as MTBE and methyl tert-amyl ether (MTAE) by the reaction of a primary alcohol with an olefin having a double bond on a tertiary carbon atom employing as catalyst an acidic zeolite having a constraint index of from about 1 to 12, e.g., zeolite ZSM-5, 11, 12, 23 dealuminized zeolite Y and rare earth-exchanged zeolite Y. European patent application No. 55,045 describes a process for reacting an olefin and an alcohol to provide an ether, e.g., isobutene and methanol to provide MTBE, in the presence of an acidic zeolite such as zeolite Beta, zeolites ZSM-5, 8, 11, 12, 23, 35, 43 and 48 and others, as Catalyst. Germany Patent No. 133,661 describes the reaction of isobutene and methanol to provide a mixture of products including MTBE, butanol and isobutene dimer in the presence of acidic zeolite Y as catalyst. According to Japan Patent No. 59-25345, a primary alcohol is reacted with a tertiary olefin in the presence of a zeolite having a silica to alumina mole ratio of at least 10 and the x-ray diffraction disclosed therein to provide a tertiary ether.

It is an object of the present invention to provide a process for converting low cost, readily available sources of light olefins to ether(s) which can be used as high octane blending stocks for gasoline.

It is another object of the invention to provide a process for catalytically converting olefin(s) in an olefin conversion unit to mixtures of alcohol(s) and ether(s) employing an acidic zeolite catalyst and thereafter recovering and recycling at least a portion of the product alcohol(s) to the olefin conversion unit to increase the overall yield of ether(s) therein.

It is a specific object of this invention to react a feed containing a substantial amount of propylene with water in an olefin conversion unit in the presence of an acidic large pore zeolite such as zeolite Beta to provide a mixture of IPA and DIPE and to recycle at least a portion of the IPA to the olefin conversion unit to increase the overall yield of DIPE.

SUMMARY OF THE INVENTION

By way of realizing the foregoing and other objects of the invention, a process is provided for producing ether containing at most relatively minor amounts of alcohol and water which comprises:

(a) contacting at least one light olefin with water and alcohol recovered from a downstream distillation operation in an olefin conversion unit in the presence of an acidic zeolite as catalyst to provide an aqueous mixture of alcohol and ether, the olefin conversion unit being operated under conditions which are effective to provide alcohol by the reaction of olefin and water therein and ether by the dehydration of alcohol and/or by the reaction of olefin and alcohol therein;

(b) introducing the aqueous mixture of alcohol and ether into a distillation unit operated under conditions which are effective to provide an azeotropic overheads fraction comprising ether and minor amounts of alcohol and water, and a bottoms fraction comprising aqueous alcohol;

(c) introducing at least a portion of the bottoms fraction into the olefin conversion unit; and, (d) introducing the azeotropic overheads fraction in an alcohol separation unit operated under conditions which are effective to provide an ether product containing at most negligible amounts of alcohol and water and an aqueous alcohol product.

By recycling alcohol to the olefin conversion unit, it is possible to increase the overall conversion of olefin to predominantly ether. This capability for directing the hydration of feed olefin to a product which is predominantly one of ether can be of particular benefit where the product is employed as an octane boost for gasoline as it eliminates or minimizes the possibility of phase separation which can occur in the case of etheric mixtures containing substantial quantities of alcohol.

DESCRIPTION OF THE PREFERRED EMBODIMENTS

Figure 1:
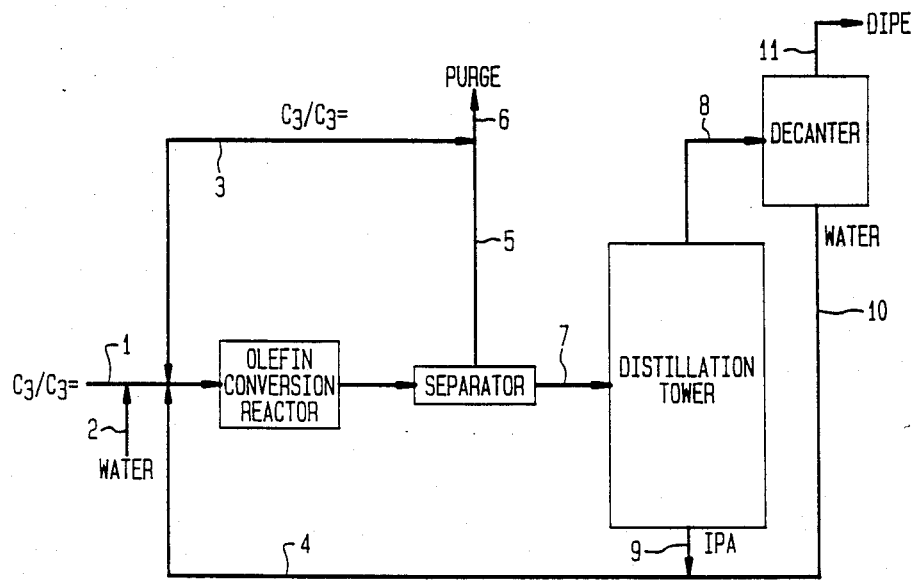
FIGS. 1 and 2 are schematic representations of various embodiments of the process of the invention as applied to the production of DIPE.

The present invention is applicable to the conversion of individual light olefins and mixtures of olefins of various structures, preferably within the $C_{2-7}$ range, to ethers. Accordingly, the invention is applicable to the conversion of ethylene, propylene, butenes, pentenes, hexenes and heptenes, mixtures of these and other olefins such as gas plant off-gas containing ethylene and propylene, naphtha cracker off-gas containing light olefins, fluidized catalytic cracked (FCC) light gasoline containing pentenes, hexenes and heptenes, refinery FCC propane/propylene streams, etc. For example, a typical FCC light olefin stream possesses the following composition:

Typical Refinery FCC Light Olefin Composition

| Typical Refinery FCC Light Olefin Composition | | |
| --- | --- | --- |
| | Wt. % | Mole % |
| Ethane | 3.3 | 5.1 |
| Ethylene | 0.7 | 1.2 |
| Propane | 14.5 | 15.3 |
| Propylene | 42.5 | 46.8 |

-continued

| Typical Refinery FCC Light Olefin Composition | | |
| --- | --- | --- |
| | Wt. % | Mole % |
| Isobutane | 12.9 | 10.3 |
| n-Butane | 3.3 | 2.6 |
| Butenes | 22.1 | 18.3 |
| Pentanes | 0.7 | 0.4 |

The process of the invention is especially applicable to the conversion of propylene and propylene-containing streams to DIPE containing at most a minor amount of IPA.

The conversion of the light olefin takes place in an olefin conversion unit wherein several reactions occur simultaneously to provide a mixture of alcohol and ether. Thus, olefin will react with water to produce alcohol, alcohol will react with olefin to produce ether and/or alcohol will undergo dehydration to produce ether.

The foregoing olefin conversion reactions can be carried out under liquid phase, vapor phase or mixed vapor-liquid phase conditions in batch or in a continuous manner under stirred tank reactor or fixed bed flow reactor conditions, e.g., trickle-bed, liquid-up-flow, liquid-down-flow, counter-current flow, co-current flow, etc.

In general, the useful olefin conversion catalysts embrace two categories of zeolite, namely, the intermediate pore size variety as represented, for example, by ZSM-5, which possess a Constraint Index of greater than about 2 and the large pore variety as represented, for example, by zeolites Y and Beta, which possess a Constraint Index no greater than about 2. Both varieties of zeolites will possess a framework silica-to-alumina ratio of greater than about 7, usually greater than at least about 20, preferably greater than at least about 200 and more preferably still, greater than about 500. The zeolite will be in the acid form and as such, will possess an alpha value of at least about 1, preferably at least about 10 and more preferably at least about 100. It will often be advantageous to provide the zeolite as a composite bound with a catalytically active or inactive material such as alumina or silica which is stable under the olefin conversion conditions employed.

Of particular interest for use herein are the large pore acidic zeolites, e.g., zeolite Beta, X, L, Y, USY, REY, Deal Y, ZSM-3, ZSM-4, ZSM-12, ZSM-20 and ZSM-50, as disclosed in commonly assigned, concurrently filed U.S. patent application Ser. No. 139,576. In accordance with said application, these large pore zeolite catalysts are used to effect the conversion of light olefin(s) to a mixture of alcohol(s) and ether(s) by contacting the olefin(s) with water in the vapor and/or liquid phase at a temperature of from about 100° to 230° C., preferably from about 120° to about 220° C. and most preferably from about 140° to about 200° C., a total system pressure of at least about 5 atm, preferably at least about 20 atm and more preferably at least about 40 atm, a water to total olefin mole ratio of from 0.1 to less than about 1.0, preferably from about 0.2 to 0.8 and most preferably from about 0.3 to 0.7 and an LHSV of from about 0.1 to about 10 in the presence of an acidic form of the zeolite. In the specific case of acidic zeolite Beta, and as described in commonly assigned, concurrently filed U.S. patent application Ser. No. (Case 4639), the contents of which are incorporated herein, the hydration conditions need not be so limited as those stated above for the case of large pore zeolites generally. Thus, use of acidic zeolite Beta can be accompanied by essentially any practical set of hydration conditions which provides alcohol(s) and ether(s) in appreciable amounts. A disclosed in said application, good results can generally be obtained employing a temperature ranging from ambient up to about 300° C., preferably from about 50° to about 220° C. and more preferably from about 90° to about 200° C., a total system pressure of at least about 5 atm, preferably at least about 20 atm and more preferably at least abut 40 atm, a water to total olefin mole ratio of from about 0.1 to about 30, preferably from about 0.2 to about 15 and most preferably from about 0.3 to about 5, and an LHSV of from about 0.1 to about 10. It may be noted that at the unusually low water:olefin mole ratios called for by the process disclosed in U.S. patent application Ser. No. (Case 4640), the production of olefin hydration products employing zeolite Beta as catalyst shifts toward ether(s) and away from alcohol(s).

The aqueous mixture of alcohol and ether produced in the olefin conversion unit, together with unconverted olefin, any inert gaseous material such as saturated hydrocarbon which may have been part of the olefin feed stream and the small quantities of oligomer which are typically present in the reaction effluent are then passed to a high pressure separator unit which is operated below the temperature of the olefin conversion unit. Two liquid phases form in the high pressure separator unit, an aqueous phase which is recycled to the olefin conversion unit and a hydrocarbon-rich phase which is flashed at lower pressure to effect separation of unconverted olefin together with any other gaseous material from the aqueous mixture of alcohol, ether and oligomer. The gaseous material is recycled to the olefin conversion unit with part of it being vented off if necessary to avoid build-up of inert gaseous components in the system. The aqueous mixture of alcohol, ether and oligomer is then introduced into a distillation tower which is preferably operated at or below atmospheric pressure to provide an azeotropic overheads fraction containing ether and minor amounts of alcohol, water and oligomer and a bottoms fraction containing water and a major part of the alcohol. Part or all of the bottoms fraction is recycled to the olefin conversion unit and the azeotropic overheads fraction, following condensation, is introduced into an alcohol separation unit which is operated under conditions effective to provide an ether-rich fraction containing oligomer, generally in an amount of less than about 10 weight percent, and little if any alcohol and water, e.g., less than about 3 weight percent, and preferably less than 2 weight percent, of these materials individually or in combination.

In one embodiment of this process, the alcohol separation unit is provided as an extraction column with process feed water serving as the extraction medium. Due to the extraction of alcohol from the ether-rich phase, the solubility of water in said phase is reduced thus leading to further loss of water from the ether product. Following extraction of the condensed azeotropic overheads from the distillation tower, the aqueous alcohol-containing extractant is advantageously introduced into the olefin conversion unit.

In another embodiment, the alcohol separation unit is provided as a decanter with the condensed azeotropic overheads separating into an ether-rich upper phase as previously described and an aqueous alcohol phase which can, if desired, be introduced into the olefin conversion unit.

The process of the invention as applied to the production of DIPE will now be discussed in connection with the process flow diagram of FIG. 1 in which a mixed propane/propylene feed ($C_3/C_3=$) is introduced through conduit 1 into an olefin conversion reaction together with water passing through conduit 2. The reactor effluent is passed to a separator unit, with part of the recovered propane/propylene mixture passing through conduit 5 being recycled through conduit 3 to the reactor and another part of the gaseous mixture being purged through conduit 6 to avoid buildup of propane in the system. The liquid products from the separator unit are passed through conduit 7 into a distillation tower which is operated under conditions which provide an azeotropic overheads containing DIPE, IPA and water together with some oligomers (mainly $C_6=$) which, following cooling, is introduced into a decanter through conduit 8. The bottoms from the distillation unit, a mixture of IPA and water, recovered through conduit 9 are recycled through conduit 4 to the olefin conversion reactor. In the decanter, separation of the distillation overheads takes place, the upper fraction comprising product DIPE, generally containing less than about 1 wt. % IPA, and the lower fraction containing mostly IPA or a mixture of IPA and water depending on the conversion level of propylene and the water to propylene mole ratio in the olefin conversion reactor.

Figure 2:
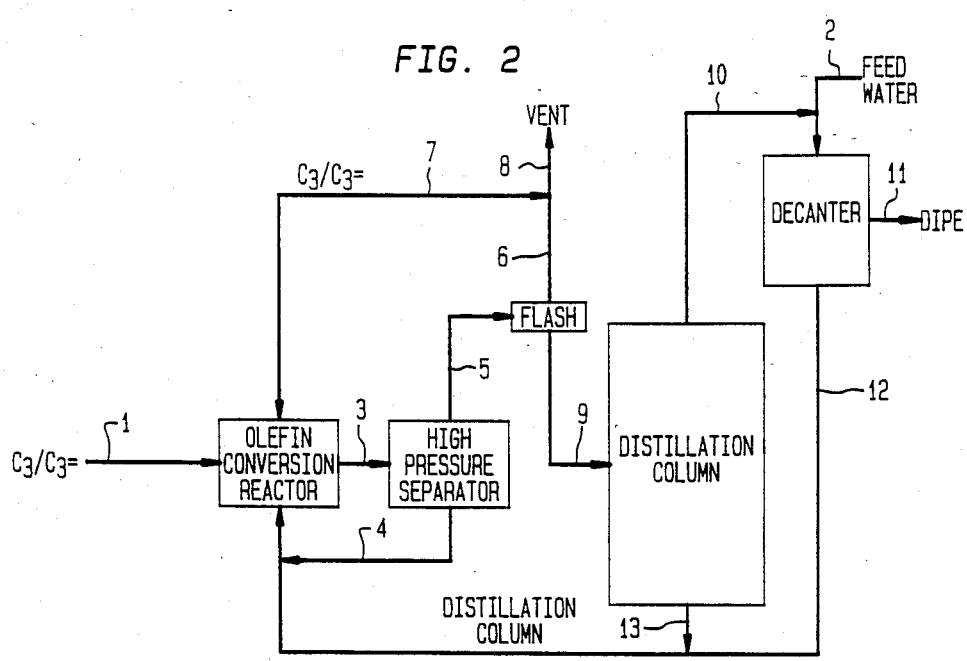

In the embodiment of the process of the invention shown in FIG. 2, a propane/propylene mixture together with recycle water originally introduced to the system through conduit 2 and other recycle streams are introduced to an olefin conversion reactor operated, e.g., with zeolite Beta at 1000-2000 psi, 280°-380° F., 0.5 WHSV propylene and a water:propylene mole ratio below 0.5. The reaction products are introduced through conduit 3 into a high pressure separator operating below reaction temperature. There, two liquid phases form with the aqueous phase being recycled to the reactor through conduit 4 and the hydrocarbon-rich phase being passed through conduit 5 to a flash unit operating at lower pressure to effect separation of the gaseous propane/propylene components. Part of the propane/propylene recovered in conduit 6 is recycled to the reactor through conduit 7 with part being vented through conduit 8 to avoid propane buildup. The flashed product in conduit 9, now containing a substantial amount of DIPE, is introduced to a distillation column preferably operating at or below atmospheric pressure. The resulting azeotropic mixture of DIPE, IPA, water and minor amounts of oligomer recovered through conduit 10 is condensed and contacted with feed water passing through conduit 2 into a decanter. Phase separation provides an essentially pure DIPE upper phase which is recovered through conduit 11 and an aqueous phase recovered through conduit 12. The aqueous phase passing through conduit 12 is combined with the aqueous bottoms from the distillation column passing through line 13 and the aqueous phase from the high pressure separator passing through line 4 to serve as recycle to the olefin conversion reactor.

The following examples are illustrative of the process of the invention.

EXAMPLE 1-4

The zeolite olefin conversion catalyst employed in these examples is zeolite Beta (82.5 wt. %) extrudate bound with colloidal silica (17.5 wt. %) employing the process of commonly assigned, copending U.S. patent application Ser. No. 44,639, filed May 1, 1987, the contents of which are incorporated by reference herein. The extrudate was prepared by thoroughly mixing the stated amounts of zeolite and colloidal silica together with a sufficient amount of water to provide an extrudable mass in the absence of any added alkali metal base and/or basic salt. Extrusion of the mass into 1/16" average diameter extrudate was followed by drying, calcining, ammonium-exchange and calcining in the conventional manner to provide an activated catalyst.

The foregoing silica-bound zeolite Beta catalyst was employed in the conversion of propylene to a mixture of IPA and DIPE under the following fixed conditions: 330° F., 1000 psig total system pressure and 0.5 weight hourly velocity (WHSV) based on propylene. The amount of IPA recycle was varied from 0.0 to 0.8, the effect of recycle on DIPE production being shown in FIG. 1 below as follows:

TABLE 1

Effect of IPA Recycle on DIPE Production

| Example | IPA WHSV | Propylene Conversion, % | DIPE Wt % Yield |
|---|---|---|---|
| 1 | 0.0 | 44 | 26 |
| 2 | 0.04 | 35 | 21 |
| 3 | 0.3 | 28 | 38 |
| 4 | 0.8 | 23 | 36 |

While propylene conversion decreases with additional alcohol recycle, as these data show, overall ether yield increases. Accordingly, it is generally advantageous to maintain a high rate of aqueous alcohol recycle from the various operations downstream from the olefin conversion unit.

EXAMPLES 5-6

These examples illustrate a vacuum distillation operation carried out under two different sets of conditions, and with the results, shown in Table 2 as follows:

TABLE 2

Vacuum Distillation Results

| Example | Pressure, torr | Boiling Pt, °F. | Condensed Overhead Composition, Wt. % | | | |
|---|---|---|---|---|---|---|
| | | | DIPE | IPA | Water | Oligomer |
| — | charge | — | 39.48 | 46.71 | 13.29 | 0.51 |
| 5 | 760 | 140 | 88.71 | 8.54 | 1.22 | 1.53 |
| 6 | 200 | 131 | 91.20 | 6.06 | 0.97 | 1.77 |

These data show that both water and IPA content in the upper layer of the condensed overhead is reduced at lower distillation pressure, and a small amount of oligomer present in the charge is concentrated in the overhead.

EXAMPLE 7

A condensed azeotropic overheads composition containing 11 wt. % water, 384 wt. % IPA, 47.3 wt. % DIPE and 3.4% oligomer was subjected to 4 successive extractions with water, and with the results, shown in Table 3 below:

TABLE 3

Multi-stage Extraction With Water

| Stage | Weight Percent Composition | | | | Yield* |
|---|---|---|---|---|---|
| | Water | IPA | DIPE | Oligomer | |
| Charge | 11.0 | 38.4 | 47.3 | 3.4 | 100.0 |
| 1 | 3.5 | 18.9 | 71.7 | 5.2 | 60.6 |
| 2 | 1.1 | 5.1 | 87.3 | 6.5 | 49.4 |
| 3 | 0.8 | 0.9 | 91.6 | 6.8 | 51.5 |
| 4 | 0.7 | 0.2 | 92.1 | 6.9 | 52.5 |

*Extraction yields are cumulative, volume recovered/volume charged.

When process water is employed in the extraction of alcohol from the IPA/DIPE azeotrope, it is generally desirable to avoid the use of large volumes of water as this would lead to the creation of a dilute IPA recycle stream.

It is within the scope of this invention to combine the foregoing aqueous extraction operation with co-extraction with other media, e.g., gasoline, which would provide a recycle stream rich in alcohol.

EXAMPLE 8

The conversion of propylene contained in a propylene/propane refinery stream is illustrated in the process scheme shown in FIG. 1. The conditions of the propylene conversion are similar to those used in Examples 1–4. The results in moles/hr of feeds/products are set forth in Table 4 below as follows:

TABLE 4

DIPE Production

| Feed/Product Stream | Moles/Hr | | | | | | | | | | | Wt % |
|---|---|---|---|---|---|---|---|---|---|---|---|---|
| | 1 | 2 | 3 | 4 | 5 | 6 | 7 | 8 | 9 | 10 | 11 | |
| Propane | 155.0 | — | 1503.0 | — | 305.3 | 155.0 | — | — | — | — | — | — |
| Propylene | 361.6 | — | 90.9 | — | 184.5 | 93.7 | — | — | — | — | — | — |
| DIPE | — | — | — | 0.1 | — | — | 122.4 | 122.4 | — | 0.1 | 122.3 | 90.1 |
| IPA | — | — | — | 101.0 | — | — | 114.4 | 14.5 | 99.9 | 1.1 | 13.4 | 5.8 |
| Oligomer | — | — | — | — | — | — | 4.9 | 4.9 | — | 4.9 | 4.9 | 3.0 |
| Water | — | 144.5 | — | 31.6 | — | — | 40.3 | 40.3 | — | 31.6 | 8.7 | 1.1 |
| | | | | | | | | | | | | 100.0 |

What is claimed is:
1. A process for producing ether containing at most negligible amounts of alcohol and water which comprises:
(a) contacting at least one light olefin with water and product alcohol recovered from a downstream distillation operation in an olefin conversion unit in the presence of an acidic zeolite as catalyst to provide an aqueous mixture of product alcohol and ether, the olefin conversion unit being operated under conditions which are effective to provide product alcohol by the reaction of olefin and water therein and ether by the dehydration of recycled product alcohol and/or by the reaction of olefin and recycled product alcohol therein;
(b) introducing the aqueous mixture of product alcohol and ether into a distillation unit operated under conditions which are effective to provide an azeotropic overheads fraction comprising ether and minor amounts of product alcohol and water, and a bottoms fraction comprising aqueous product alcohol;

(c) introducing at least a portion of the bottoms fraction comprising aqueous product alcohol into the olefin conversion unit; and, (d) introducing the azeotropic overheads fraction comprising ether and minor amounts of product alcohol and water in a product alcohol separation unit operated under conditions which are effective to provide an ether product containing at most negligible amounts of product alcohol, and aqueous product alcohol, provided, the rate of introduction of product alcohol into the olefin conversion unit is sufficiently high as to increase the overall yield of ether.

2. The process of claim 1 wherein the zeolite possesses a Constraint Index of no greater than about 2.

3. The process of claim 1 wherein the zeolite is selected from the group consisting of zeolite Beta, X, L, Y, REY, Deal Y, ZSM-3, ZSM-4, ZSM-12, ZSM-20 and ZSM-50.

4. The process of claim 1 wherein the zeolite is composited with a binder.

5. The process of claim 1 wherein the zeolite is composited with a binder selected from the group consisting of alumina and silica.

6. The process of claim 1 wherein the light olefin is at least one member of the group consisting of ethylene, propylene, butenes, pentenes, hexenes and heptenes.

7. The process of claim 1 wherein the olefin conversion unit is maintained under conditions comprising a temperature of from ambient to about 300° C., an overall system pressure of at least about 5 atm, a water to total olefin mole ratio of from about 0.1 to about 30 and an LHSV of from about 0.1 to about 10.

8. The process of claim 1 wherein the zeolite is zeolite Beta and the water to total olefin mole ratio is less than about 1.

9. The process of claim 1 wherein effluent from the olefin conversion unit containing unconverted olefin and, optionally, inert gaseous hydrocarbon, is introduced into a separator unit operated under conditions which are effective to provide a hydrocarbon fraction containing ether, a small amount of alcohol, water, unconverted olefin and inert hydrocarbon, if any, and an aqueous alcohol fraction, the hydrocarbon fraction being flashed at reduced pressure to release unconverted olefin and inert gaseous hydrocarbon prior to introduction of the remaining components of said fraction into the distillation unit.

10. The process of claim 9 wherein unconverted olefin is introduced into the olefin conversion unit.

11. The process of claim 1 wherein the distillation unit is operated at atmospheric pressure or below.

12. The process of claim 1 wherein the alcohol separation unit is provided as an extraction apparatus employing water as the extraction agent.

13. The process of claim 12 wherein following extraction of the azeotropic overheads fraction, all or part of the recovered water containing alcohol is introduced to the olefin conversion unit.

14. The process of claim 1 wherein the alcohol separation unit is provided as a decantation apparatus providing an upper ether-rich phase and a lower aqueous alcohol phase.

15. The process of claim 14 wherein all or part of the aqueous alcohol phase is introduced into the olefin conversion unit.

16. The process of claim 1 wherein the olefin is propylene or propylene in admixture with propane and the final product is diisopropyl ether containing less than about 10 weight percent oligomer and less than 3 weight percent of combined isopropyl alcohol and water.

17. The process of claim 1 wherein the olefin conversion unit is subdivided into two or more reaction zones operated under the same or different olefin conversion conditions and containing the same or different acidic zeolite as catalyst.

18. The process of claim 17 wherein the olefin conversion unit is subdivided into at least two reaction zones, the first of said reaction zones being operated under conditions which are conducive to the production of alcohol therein and the second reaction zone being operated under conditions which are conducive to the production of ether therein.

19. A process for producing diisopropyl ether containing at most negligible amounts of isopropyl alcohol and water which comprises (a) contacting propylene with water and product isopropyl alcohol recovered from a downstream distillation operation in a propylene conversion unit in the presence of an acidic zeolite as catalyst to provide an aqueous mixture of product isopropyl alcohol and diisopropyl ether, the propylene conversion unit being operated under conditions which are effective to provide product isopropyl alcohol by the reaction of propylene and water therein and diisopropyl ether by the dehydration of recycled product isopropyl alcohol and/or by the reaction of propylene and recycled product isopropyl alcohol therein;

(b) introducing the aqueous mixture of product isopropyl alcohol and diisopropyl ether into a distillation unit operated under conditions which are effective to provide an azeotropic overheads fraction comprising diisopropyl ether and minor amounts of product isopropyl alcohol, and a bottom fraction comprising aqueous product isopropyl alcohol;

(c) introducing at least a portion of the bottoms fraction comprising aqueous product isopropyl alcohol into the propylene conversion unit; and, (d) introducing the azeotropic overheads fraction comprising a diisopropyl ether and minor amount of product isopropyl alcohol and water in a product isopropyl alcohol separation unit operated under conditions which are effective to provide diisopropyl ether product containing at most negligible amounts of product isopropyl alcohol, and aqueous isopropyl alcohol, provided, the rate of introduction of product isopropyl alcohol into the propylene conversion unit is sufficiently high as to increase the overall yield of diisopropyl ether.

20. The process of claim 19 wherein the zeolite possesses a Constraint Index of no greater than about 2.

21. The process of claim 19 wherein the zeolite is selected from the group consisting of zeolite Beta, X, L, Y, REY, Deal Y, ZSM-3, ZSM-4, ZSM-12, ZSM-20 and ZSM-50.

22. The process of claim 19 wherein the propylene conversion unit is maintained under conditions comprising a temperature of from ambient to about 300° C., an overall system pressure of at least about 5 atm, a water to total olefin mole ratio of from about 0.1 to about 30 and an LHSV of from about 0.1 to about 10.

23. The process of claim 19 wherein the zeolite is zeolite Beta and the water to propylene mole ratio is less than about 1.

24. The process of claim 19 wherein effluent from the propylene conversion unit containing unconverted propylene and, optionally, inert gaseous hydrocarbon, is introduced into a separator unit operated under conditions which are effective to provide a hydrocarbon fraction containing diisopropyl ether, a small amount of product isopropyl alcohol, water, unconverted propylene and inert hydrocarbon, if any, and an aqueous product isopropyl alcohol fraction, the hydrocarbon fraction being flashed at reduced pressure to release unconverted propylene and inert gaseous hydrocarbon, if any, prior to introduction of the remaining components of said fraction into the distillation unit.

25. The process of claim 19 wherein the distillation unit is operated at atmospheric pressure or below.

26. The process of claim 19 wherein the product isopropyl alcohol separation unit is provided as an extraction apparatus employing water as the extraction agent.

27. The process of claim 26 wherein following extraction of the azeotropic overheads fraction, all or part of the recovered water containing product isopropyl alcohol is introduced to the propylene conversion unit.

28. The process of claim 1 wherein the product isopropyl alcohol separation unit is provided as a decantation apparatus providing an upper diisopropyl ether-rich phase and a lower aqueous isopropyl alcohol phase.

29. The process of claim 28 wherein all or part of the aqueous isopropyl alcohol phase is introduced into the propylene conversion unit.

* * * * *